US008787739B2

(12) United States Patent
Hsiao

(10) Patent No.: US 8,787,739 B2
(45) Date of Patent: Jul. 22, 2014

(54) AROMA DIFFUSER HAVING A VARIABLE PLUGGING DEVICE USING AN AROMA STONE

(71) Applicant: Serene House International Enterprise Ltd., Road Town (VG)

(72) Inventor: Ming Jen Hsiao, Miaoli County (TW)

(73) Assignee: Serene House International Enterprise Ltd. (VG)

( * ) Notice: Subject to any disclaimer, the term of this patent is extended or adjusted under 35 U.S.C. 154(b) by 0 days.

(21) Appl. No.: 13/669,411

(22) Filed: Nov. 5, 2012

(65) Prior Publication Data

US 2014/0124594 A1    May 8, 2014

(51) Int. Cl.
*A61L 9/03*    (2006.01)
(52) U.S. Cl.
USPC .......................................................... 392/390
(58) Field of Classification Search
USPC .............. 392/390; 4/252.4; 285/56; 239/129; 320/107
See application file for complete search history.

(56) References Cited

U.S. PATENT DOCUMENTS

| 3,587,968 | A | * | 6/1971 | Aubervilliers et al. | 239/47 |
| 5,647,052 | A | * | 7/1997 | Patel et al. | 392/390 |
| 6,435,563 | B2 | * | 8/2002 | Phillips | 285/56 |
| D604,699 | S | * | 11/2009 | Yamamoto | D13/144 |
| 8,066,420 | B2 | | 11/2011 | Hsiao | |
| 8,068,725 | B2 | * | 11/2011 | Cheung | 392/394 |
| 8,147,116 | B1 | | 4/2012 | Hsiao | |
| 8,262,277 | B2 | | 9/2012 | Hsiao | |
| 8,265,465 | B2 | * | 9/2012 | Jorgensen | 392/386 |

FOREIGN PATENT DOCUMENTS

JP    02369705 A  *  12/2002

* cited by examiner

*Primary Examiner* — Dana Ross
*Assistant Examiner* — Renee L Miller
(74) *Attorney, Agent, or Firm* — Chun-Ming Shih

(57) ABSTRACT

An aroma diffuser is provided, including: a diffuser having a hollow housing, a heat conduction container disposed in the hollow housing, a resistor disposed under the heat conduction container, and a plugging device installed in a second opening of the hollow housing and electrically connected to the resistor; and an aroma stone disposed in the heat conduction container that absorbs essential oil. The aroma stone can be disposed after the essential oil evaporates completely. The plugging device is a car plug that can be combined with an aroma stone used in a car; or a USB device that can be combined with a mobile device, a notebook computer, a desktop computer or any appliance with a USB connection port. When supplied with power, the resistor generates heat, and the heat conduction container conducts the heat to the aroma stone for the aroma stone to diffuse scent.

10 Claims, 4 Drawing Sheets

AROMA DIFFUSER HAVING A VARIABLE PLUGGING DEVICE USING AN AROMA STONE

CROSS-REFERENCES TO RELATED APPLICATION

Two pending new application Ser. Nos. 13/543,490 and 13/549,493 filed on Jul. 15, 2012 are hereby incorporated by reference.

BACKGROUND OF THE INVENTION

1. Field of the Invention

This invention relates to aroma diffusers, and, more particularly, to an aroma diffuser having a variable plugging device using an aroma stone.

2. Description of Related Art

U.S. Pat. Nos. 8,066,420, 8,262,277 and 8,147,116 disclose an aroma diffuser, which includes a power supply, a lamp, essential oil or aroma wax, and a container for the aroma wax to be contained therein. After the aroma wax contained in the container is evaporated completely and before new aroma wax is placed in the container, a user needs to take aroma wax residues out from the container. The user is likely to be stained by the aroma wax residues.

However, the aroma diffuser cannot be supplied with other sources of power, such as power supplied by a car or a mobile device, and cannot be taken with the user anywhere.

SUMMARY OF THE INVENTION

In view of the problems of the prior art, the present invention provides an aroma diffuser having a variable plugging device using an aroma stone. The aroma diffuser may include a car plug or a USB device, and can be supplied with power from different sources. The aroma stone is disposable. After essential oil absorbed by the aroma stone evaporates completely, the aroma stoned can be disposed. Therefore, the aroma diffuser is thus safe and convenient to use.

In an embodiment, the aroma diffuser comprises: a diffuser including a hollow housing, a heat conduction container, a resistor, and a plugging device, wherein the hollow housing has a first opening and a second opening, the heat conduction container is received in the hollow housing and has a free end, the resistor is disposed under the heat conduction container, and the plugging device is installed in the second opening of the hollow housing and electrically connected to the resistor; and an aroma stone disposed in the heat conduction container, wherein the resistor, when supplied with power, generates heat, and the heat conduction container conducts the heat to the aroma stone for the aroma stone to diffuse scent. The aroma stone comprises a plurality of pores and a liquid aroma material absorbed by the pores and limited to flow in the pores only. Therefore, if the aroma diffuser is toppled and broken by chance, the liquid aroma material absorbed by the pores will not flow out from the heat conduction container and be in contact with power supplied to the resistor. The essential oil thus will not pollute the environment or the interior decoration of a car. The essential oil, since absorbed by and staying in the pores of the aroma stone, can have assured quality and will not be in contact with air in the ambient and evaporate quickly.

In a embodiment, the aroma stone is made of porous ceramic, gypsum, a fiber block, porous heat-resistant plastic, a soapstone, paper, porous earth, or wood.

In an embodiment the liquid aroma material is essential oil, essence, flower essence or perfume.

Since the liquid aroma material is absorbed by the pores of the aroma stone, if the aroma diffuser is toppled by chance, the liquid aroma material will not from out from the heat conduction container or flow to the resistor or any space. Therefore, the aroma diffuser is safe to use. Since the aroma stone is disposable after the essential oil evaporates completely, it is convenient for a user to change the aroma stone. In an embodiment, the plugging device comprises a car plug or a USB device, and can be supplied with power from different sources.

BRIEF DESCRIPTION OF DRAWINGS

The invention can be more fully understood by reading the following detailed description of the preferred embodiments, with reference made to the accompanying drawings, wherein.

DETAILED DESCRIPTION OF THE INVENTION

The following illustrative embodiments are provided to illustrate the disclosure of the present invention, these and other advantages and effects can be apparently understood by those in the art after reading the disclosure of this specification. The present invention can also be performed or applied by other different embodiments. The details of the specification may be on the basis of different points and applications, and numerous modifications and variations can be devised without departing from the spirit of the present invention.

Figure 1:
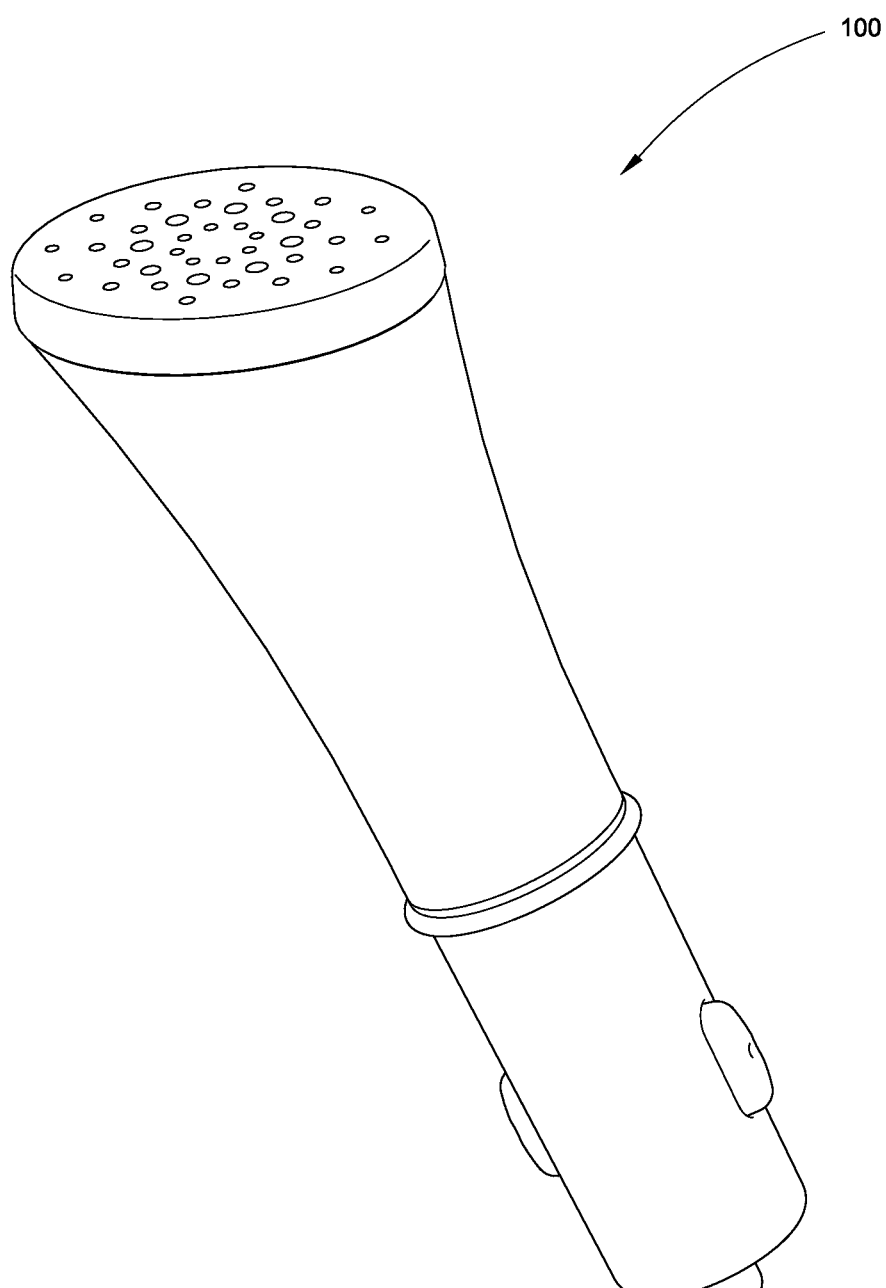
FIG. 1 is a schematic diagram of an aroma diffuser having a variable plugging device using an aroma stone of an embodiment according to the present invention.
Figure 2:
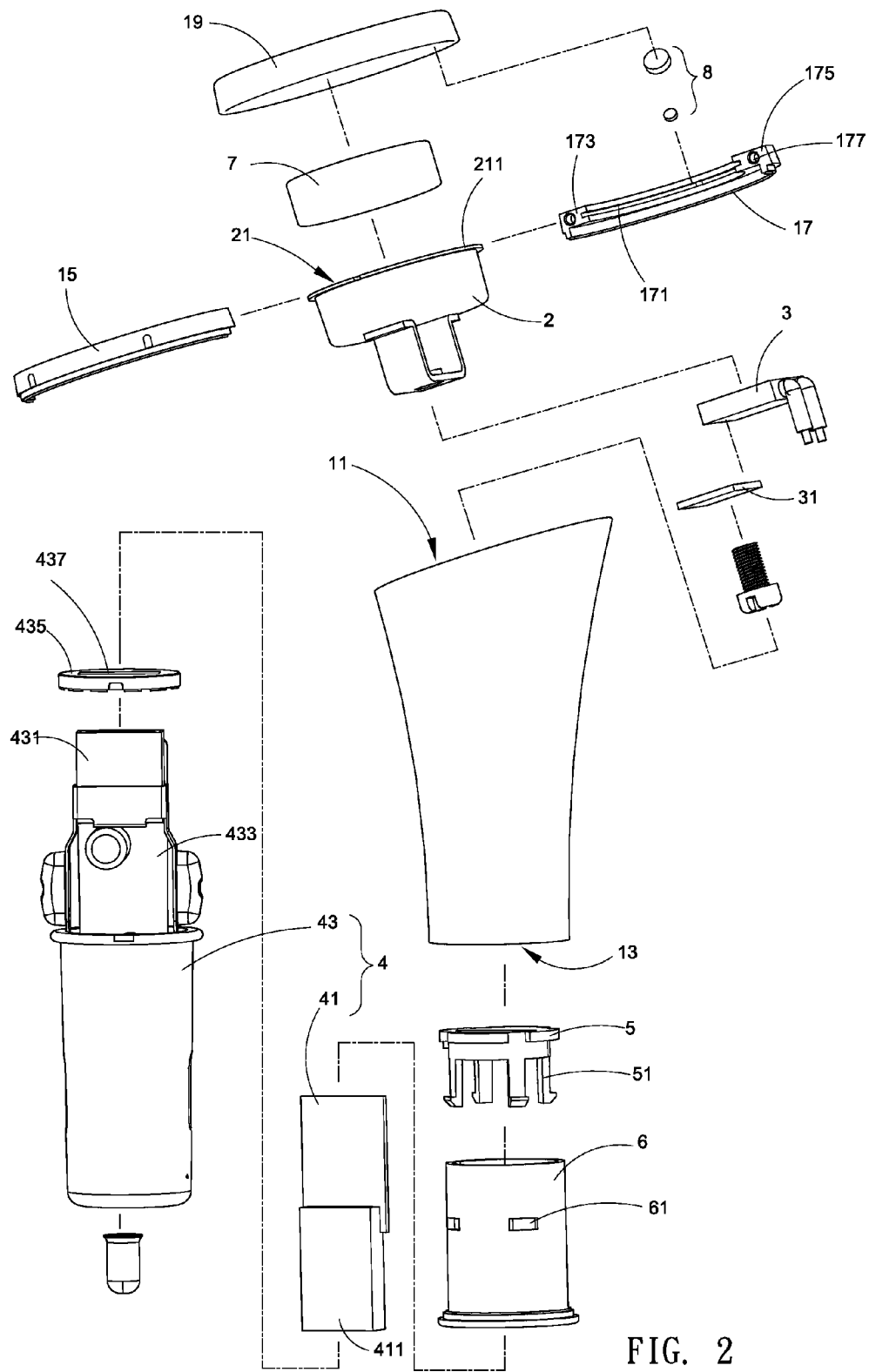
FIG. 2 is an exploded view of the aroma diffuser shown in FIG. 1.
Figure 3:
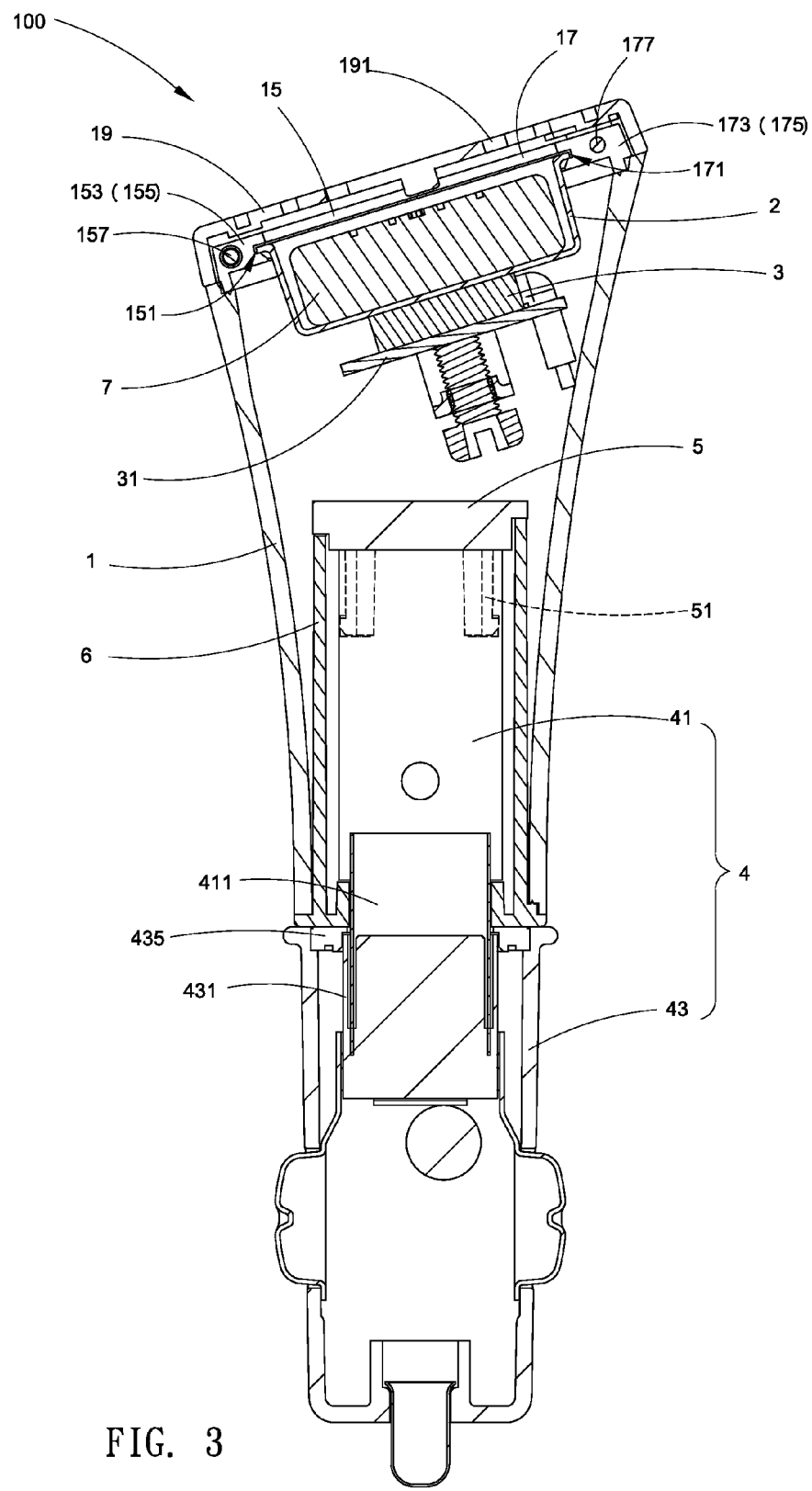
FIG. 3 is a cross-sectional view of the aroma diffuser shown in FIG. 1.

Referring to FIGS. 1-3, an aroma diffuser 100 comprises a hollow housing 1, a heat conduction container 2, a resistor 3, and a plugging device 4. The hollow housing 1 has a first opening 11 and a second opening 13. The heat conduction container 2 is installed in the hollow housing 1 and has a free end 21. The resistor 3 is installed under the heat conduction container 2. The plugging device 4 is installed in the second opening 13 of hollow housing 1 and electrically connected (not shown) to the resistor 3.

The aroma diffuser 100 further comprises an aroma stone 7 disposed in the heat conduction container 2.

When supplied with power, the resistor 3 generates heat, and the heat conduction container 2 conducts the heat to the aroma atone 7 for the aroma stone 7 to diffuse scent.

In an embodiment, the aroma stone 7 is made of porous ceramic, gypsum, a fiber block, porous heat-resistant plastic, a soapstone, paper, porous earth, or wood.

In an embodiment the liquid aroma material absorbed by the pores of the aroma stone 7 is essential oil, essence, flower essence or perfume.

In a preferable embodiment, the aroma stone 7 is a porous ceramic that has essential oil absorbed thereby. The resistor 3 generates heat, and the heat will heat the aroma stone 7 and evaporate the essential oil into the ambient.

Since the aroma stone 7 is solid and porous, essential oil will be absorbed by and stay in the aroma stone 7. When placing a new aroma stone 7 in the heat conduction container 2 that diffuses different scent from the previous one disposed in the heat conduction container 2, a user will not be stained by the essential oil absorbed by the aroma stone 7. As the aroma diffuser 100 is toppled by chance, the essential oil will not flow out from the heat conduction container 2 or flow to the resistor 2 or any space. Therefore, the aroma diffuser 100 is safe to use.

In an embodiment, referring to FIGS. 1-3, the aroma diffuser 100 further comprises a first hooking ring 15, a second hooking ring 17, a cover 19, a first inner annular groove 151 formed on an inner side of the first hooking ring 15, and a second inner annular groove 171 formed on an inner side of the second hooking ring 17. An outer flange 211 is formed on the free end of the heat conduction container 2, and has one side hooked to the first inner annular groove 151 of the first hooking ring 15 and the other side hooked to the second inner annular groove 171 of the second hooking ring 17. The cover 19 covers and fixes outer peripheries of the first hooking ring 15 and the second hooking ring 17, and comprises air vents 191.

In an embodiment, the aroma diffuser 100 further comprises a pawl 5 and a hollow tail cover 6. The pawl 5 has a plurality of hooking components 51 protruding downward therefrom. The hollow tail cover 6 has a plurality of perforations 61 disposed on a periphery thereof. The pawl 5 is combined with an inner portion of the hollow tail cover 6. The hooking components 51 of the pawl 5 are hooked outward to the perforations 61. The hollow tail cover 6 is combined with an inner side of the second opening 13 of the hollow housing 1. The plugging device 4 comprises a USB device 41 (referring to FIG. 4 at the same time). The USB device 41 has one side combined with the hollow tail cover 6 and the pawl 5 and electrically connected to the resistor 3, and a USB male connector 411 disposed on the other side protruding from the second opening 13 of the hollow housing 1. The USB male connector 411 can be combined with an external USB connection port (e.g., a USB female connector of a mobile device or a computer) that provides power to the resistor 3, and the resistor 3 can generate heat, which will be conducted by the heat conduction container 2 to the aroma stone 7.

Figure 4:
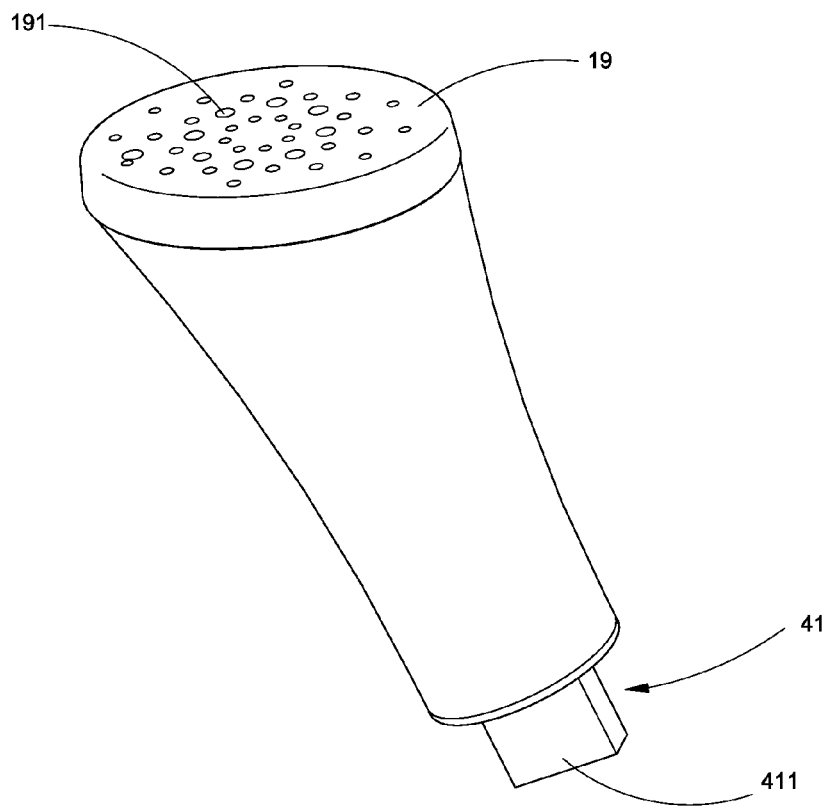
FIG. 4 is a schematic diagram of an aroma diffuser having a variable plugging device using an aroma stone according to the present invention, wherein the aroma diffuser employs a USB device and a USB male connector.
Figure 5:
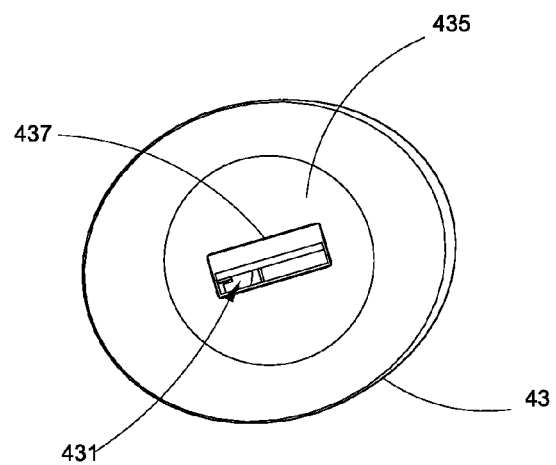
FIG. 5 is a schematic diagram of an aroma diffuser having a variable plugging device using an aroma stone according to the present invention, wherein a car plug having an end portion combined with a USB female connector is provided.

Please refer to FIGS. 2, 4 and 5 at the same time. In an embodiment, the plugging device 4 comprises a car plug 43, and the car plug 43 comprises a USB female connector 431 installed on one end thereof, and a PCB 433 installed inside the car plug 43 and electrically connected to the USB female connector 431. The USB male connector 411 that protrudes from the second opening 13 of the hollow housing 1 is detachably electrically connected to the USB female connector 431 of the car plug 43, thus forming an aroma diffuser having a variable plugging device using an aroma stone. When the car plug 43 is not in use, the car plug 43 can be separated from the USB male connector 411 at one side of the USB female connector 431, and the second opening 13 of the hollow housing 1 exposes the USB male connector 411, which can be connected to a USB connection port.

In an embodiment, the PCB 433 supplies power to the resistor 3 intermittently, and the aroma diffuser 100 that uses the aroma stone 7 diffuses scent intermittently.

Please refer to FIGS. 2 and 3. The car plug 43 further comprises an interface cover 435. The interface cover 435 has a through hole 437 formed at a center thereof. The interface cover 435 corresponds to the USB female connector and is connected to one end of the car plug 43.

In an embodiment, the plugging device 4 is the USB device 41 (referring to FIG. 4) or the car plug 43 (referring to FIG. 1). The USB device 41 is electrically connected to the resistor 3. The USB male connector 411 of the USB device 41 can be electrically connected to a USB female connector of a mobile device or a computer (not shown). The car plug 43 can be electrically connected to the resistor 3. The car plug 43 is plugged into an in-car electrical connector.

In an embodiment, referring to FIGS. 2 and 3, the resistor 3 is a metal resistor such as a positive temperature coefficient (PTC) resistor. In an embodiment, the bottom portion of the resistor 3 is further combined with a washer 31 to protect the resistor 3.

In an embodiment, the first hooking ring 15 comprises a first end portion 153 and a second end portion 155, one of which comprises a protruding tenon 157, and the second hooking ring 17 comprises a first end portion 173 and a second end portion 175, one of which comprises a mortise 177 that can be combined with the tenon 157.

In an embodiment, the heat conduction container 5 and the aroma stone 7 have matched sizes and shapes, in order for the aroma stone 7 to be contained in the heat conduction container 5 and the heat conductive container 5 to conduct heat to the aroma stone 7 effectively.

In an embodiment, the cover 19 and the first hooking ring 15 or second hooking ring 17 can be combined with magnets 8 such that the magnets 8 attract one another and the cover 19 can cover and be fixed to the first hooking ring 15 or the second hooking ring 17. Therefore, the cover 19 can cover the first hooking ring 15 or the second hooking ring and the first opening 11 of the hollow housing 1 easily.

In an embodiment, the car plug 43 can be combined with an aroma material and used in a car. In an embodiment, the USB device 41 can be used in a mobile device, a notebook computer, a desktop computer and any appliance that has a USB connection port. Therefore, a user can use the aroma diffuser with a variety of plugging devices. A user is allowed to lift the sealing cover 72, and place the aroma stone in the heat conduction container 2. The aroma diffuser 100 of the present invention can be safely used in a car or used by a mobile device or a notebook computer that has a USB connection port.

The foregoing descriptions of the detailed embodiments are only illustrated to disclose the features and functions of the present invention and not restrictive of the scope of the present invention. It should be understood to those in the art that all modifications and variations according to the spirit and principle in the disclosure of the present invention should fall within the scope of the appended claims.

What is claimed is:

1. An aroma diffuser, comprising:
a diffuser including a hollow housing, a heat conduction container, a resistor, and a plugging device, wherein the hollow housing has a first opening and a second opening at opposite ends, respectively, the heat conduction container is received in the hollow housing and has a free end, the resistor is disposed under the heat conduction container, and the plugging device is installed in the second opening of the hollow housing and electrically connected to the resistor; and
an aroma stone disposed in the heat conduction container, wherein the resistor, when supplied with power, generates heat, and the heat conduction container conducts the heat to the aroma stone for the aroma stone to diffuse scent, wherein the diffuser further comprises a first hooking ring, a second hooking ring, a cover, a first inner annular groove formed in an inner side of the first hooking ring, and a second inner annular groove formed in an inner side of the second hooking ring, the heat conduction container has an outer flange disposed on the free end and having one side hooked to the first inner annular groove of the first hooking ring and the other side hooked to the second inner annular groove of the second hooking ring, and the cover has air vents and covers and fixes outer peripheries of the first hooking ring and the second hooking ring, wherein the diffuser further comprises a cylindrical hollow tail cover having a plurality of perforations installed on an outer periphery thereof and a cylindrical pawl having a plurality of hooking components extending downward therefrom, the cylindrical hollow tail cover is received in the second opening of the hollow housing and the cylindrical pawl is installed at one distal end of the cylindrical hollow tail cover, and the plugging device installed on the other distal end of the cylindrical hollow tail cover comprises a USB device, one side of which is combined inside the cylindrical hollow tail cover and with the pawl and electrically connected to the resistor, the USB device having a USB male connector disposed on other side of the plugging device to protrude from the second opening of the hollow housing.

2. The aroma diffuser of claim 1, wherein the aroma stone comprises a plurality of pores and a liquid aroma material absorbed by the pores.

3. The aroma diffuser of claim 2, wherein the liquid aroma material is essential oil, essence, flower essence or perfume.

4. The aroma diffuser of claim 1, wherein the aroma stone is made of a porous ceramic, gypsum, a fiber block, porous heat-resistant plastic, a soapstone, paper, porous earth, or wood.

5. The aroma diffuser of claim 2, wherein the aroma stone is made of a porous ceramic, gypsum, a fiber block, porous heat-resistant plastic, a soapstone, paper, porous earth, or wood.

6. The aroma diffuser of claim 1, wherein the cover and the first hooking ring or the second hooking ring are combined with magnets such that the magnets attract one another and the cover is fixed to the first hooking ring or the second hooking ring.

7. The aroma diffuser of claim 1, wherein the first hooking ring comprises a first end portion and a second end portion, one of which is provided with a protruding tenon, and the second hooking ring comprises a first end portion and a second end portion, one of which is provided with a mortise that is combined with the tenon.

8. The aroma diffuser of claim 1, wherein the plugging device further comprises a car plug having a PCB installed inside the car plug and a USB female connector connected to one end of the car plug and electrically connected to the PCB, and the USB male connector protruding from the second opening of the hollow housing is detachably electrically connected to the USB female connector of the car plug, such that the car plug can be separated from the USB male connector from one end of the USB female connector when the car plug is not in use and the USB male connector is exposed from the second opening of the hollow housing for use as a USB connection port.

9. The aroma diffuser of claim 8, wherein the car plug comprises an interface cover having a through hole formed at a center thereof, the interface cover corresponding to the USB female connector and connected to one end of the car plug.

10. The aroma diffuser of claim 1, further comprising a washer combined with a bottom portion of the resistor to protect the resistor.

* * * * *